(12) United States Patent
McCombie et al.

(10) Patent No.: US 10,238,338 B2
(45) Date of Patent: *Mar. 26, 2019

(54) MODULAR WRIST-WORN PROCESSOR FOR PATIENT MONITORING

(71) Applicant: SOTERA WIRELESS, INC., San Diego, CA (US)

(72) Inventors: Devin McCombie, San Diego, CA (US); Gunnar Trommer, Encinitas, CA (US); Jim Moon, San Diego, CA (US); Marshal Dhillon, San Diego, CA (US); Scott Clear, Escondido, CA (US); Julian Groeli, San Diego, CA (US)

(73) Assignee: SOTERA WIRELESS, INC., San Diego, CA (US)

( * ) Notice: Subject to any disclaimer, the term of this patent is extended or adjusted under 35 U.S.C. 154(b) by 66 days.

This patent is subject to a terminal disclaimer.

(21) Appl. No.: 15/263,277

(22) Filed: Sep. 12, 2016

(65) Prior Publication Data

US 2017/0224281 A1     Aug. 10, 2017

Related U.S. Application Data

(63) Continuation of application No. 13/399,616, filed on Feb. 17, 2012, now Pat. No. 9,439,574.

(Continued)

(51) Int. Cl.
*A61B 5/00* (2006.01)
*G06F 19/00* (2018.01)

(Continued)

(52) U.S. Cl.
CPC .......... *A61B 5/6831* (2013.01); *A61B 5/0022* (2013.01); *A61B 5/0024* (2013.01); *A61B 5/0059* (2013.01); *A61B 5/029* (2013.01); *A61B 5/02055* (2013.01); *A61B 5/02427* (2013.01); *A61B 5/0404* (2013.01); *A61B 5/6824* (2013.01); *A61B 5/6826* (2013.01); *A61B 5/742* (2013.01); *A61B 5/749* (2013.01); *A61B 5/7465* (2013.01); *G06F 1/163* (2013.01);

(Continued)

(58) Field of Classification Search
None
See application file for complete search history.

(56) References Cited

U.S. PATENT DOCUMENTS 6,468,222 B1 * 10/2002 Mault .................. A61B 5/0833
                                                            600/529
6,478,736 B1 * 11/2002 Mault .................... G16H 15/00
                                                            600/300

(Continued)

*Primary Examiner* — John R Downey
*Assistant Examiner* — Shirley Jian
(74) *Attorney, Agent, or Firm* — Acuity Law Group, PC; Michael A. Whittaker

(57) ABSTRACT

The invention provides a physiological probe that comfortably attaches to the base of the patient's thumb, thereby freeing up their fingers for conventional activities in a hospital, such as reading and eating. The probe, which comprises a separate cradle module and sensor module, secures to the thumb and measures time-dependent signals corresponding to LEDs operating near 660 and 905 nm. The cradle module, which contains elements subject to wear, is preferably provided as a disposable unit.

17 Claims, 9 Drawing Sheets

Related U.S. Application Data

(60) Provisional application No. 61/444,285, filed on Feb. 18, 2011.

(51) Int. Cl.
  *A61B 5/024* (2006.01)
  *G16H 40/63* (2018.01)
  *A61B 5/0205* (2006.01)
  *A61B 5/029* (2006.01)
  *A61B 5/0404* (2006.01)
  *G06F 1/16* (2006.01)
  *A61B 5/021* (2006.01)
  *A61B 5/053* (2006.01)
  *A61B 5/08* (2006.01)
  *A61B 5/11* (2006.01)
  *A61B 5/145* (2006.01)

(52) U.S. Cl.
  CPC .......... *G06F 19/00* (2013.01); *G16H 40/63* (2018.01); *A61B 5/021* (2013.01); *A61B 5/02438* (2013.01); *A61B 5/053* (2013.01); *A61B 5/0816* (2013.01); *A61B 5/1116* (2013.01); *A61B 5/1118* (2013.01); *A61B 5/14542* (2013.01); *A61B 2505/03* (2013.01); *A61B 2560/045* (2013.01); *A61B 2560/0412* (2013.01); *A61B 2560/0443* (2013.01); *A61B 2562/0219* (2013.01); *A61B 2562/0238* (2013.01); *A61B 2562/222* (2013.01); *A61B 2562/227* (2013.01)

(56) References Cited

U.S. PATENT DOCUMENTS

| | | | |
|---|---|---|---|
| 6,605,038 B1* | 8/2003 | Teller | A61B 5/411 600/300 |
| 6,790,178 B1* | 9/2004 | Mault | A61B 5/0011 128/903 |
| 7,020,508 B2* | 3/2006 | Stivoric | A61B 5/0205 600/390 |
| 7,479,041 B1* | 1/2009 | Chen | H01R 13/60 439/528 |
| 2010/0261988 A1* | 10/2010 | Tamir | A61B 5/14546 600/365 |
| 2011/0224498 A1* | 9/2011 | Banet | A61B 5/00 600/300 |
| 2012/0296174 A1* | 11/2012 | McCombie | A61B 5/02427 600/301 |

* cited by examiner

A

B

A

B

MODULAR WRIST-WORN PROCESSOR FOR PATIENT MONITORING

RELATED APPLICATIONS

The present application is a continuation of U.S. patent application Ser. No. 13/399,616 filed Feb. 17, 2012, now U.S. Pat. No. 9,439,574, issued Sep. 13, 2016, which claims the benefit of priority to U.S. Provisional Application No. 61/444,285, filed Feb. 18, 2011, each of which is hereby incorporated by reference, including the drawings.

BACKGROUND OF THE INVENTION

The following discussion of the background of the invention is merely provided to aid the reader in understanding the invention and is not admitted to describe or constitute prior art to the present invention.

Blood pressure is a vital sign often considered to be a good indicator of a patient's health. In critical care environments like the ICU and OR, blood pressure can be continuously monitored with an arterial catheter inserted in the patient's radial or femoral artery. Alternatively, blood pressure can be measured intermittently with a cuff using oscillometry, or manually by a medical professional using auscultation. Many patient monitors perform both the catheter and cuff-based measurements of blood pressure.

Blood pressure can also be monitored continuously with a technique called pulse transit time (PTT), defined as the transit time for a pressure pulse launched by a heartbeat in a patient's arterial system. Typical PTT measurements determine the time separating a maximum point on the QRS complex (indicating the peak of ventricular depolarization) and a foot of the PPG waveform (indicating the arriving pressure pulse). PTT depends primarily on arterial compliance, the propagation distance of the pressure pulse (which is closely approximated by the patient's arm length), and blood pressure.

PTT has been shown in a number of studies to correlate to systolic (SYS), diastolic (DIA), and mean (MAP) blood pressures. PTT can be measured with a patient monitor that includes separate modules to determine both an electrocardiogram (ECG) and SpO2. During a PTT measurement, multiple electrodes typically attach to a patient's chest to determine a time-dependent ECG component characterized by a sharp spike called the 'QRS complex'. The QRS complex indicates an initial depolarization of ventricles within the heart and, informally, marks the beginning of the heartbeat and a pressure pulse that follows. International Patent Application No. PCT/US2010/048866, which is hereby incorporated by reference in its entirety, describes a body-worn monitor that continuously measures a plurality of vital signs from a patient. The body-worn monitor features a series of sensors that attach to the patient to measure time-dependent PPG, ECG, accelerometer-based motion (ACC), oscillometric (OSC), respiratory rate (RR), and impedance pneumography (IP) waveforms. A wrist-worn microprocessor (CPU) continuously processes these waveforms to determine the patient's vital signs, degree of motion, posture and activity level. Sensors that measure these signals typically send digitized information to a wrist-worn transceiver through a serial interface, or bus, operating on a controlled area network (CAN) protocol. The CAN bus is typically used in the automotive industry, which allows different electronic systems to effectively and robustly communicate with each other with a small number of dropped packets, even in the presence of electrically noisy environments. This is particularly advantageous for ambulatory patients that may generate signals with large amounts of motion-induced noise.

It is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

SUMMARY OF THE INVENTION

It is an object of the present invention to provide a body-worn data processing system for determining/monitoring physiological properties of the wearer. The system comprises a housing which contains the processor module, and a separate plastic casing which receives the housing. The processor module is sealed in a water-proof plastic fashion within the housing, which provides openings to access electrical interconnects operably connected to the processor module. During operation, the housing snaps into a separate plastic base (or "cradle"). Upon mating of the housing and the base, interface cavities, or "ports," are formed for receiving the terminal ends of data cables leading to and/or from one or more sensors which collect data related to the physiological properties of interest. The ports may also provide connection to one or more peripheral devices such as blood pressure cuffs, wireless communication hardware, etc. Insertion of a terminal end into such a port establishes electrical communication between the port's corresponding electrical interconnects and the cable, thereby permitting electrical communication between the processor module and the corresponding sensor or peripheral device. In certain embodiments, the communications between the processor, sensors, and any peripherals connected through the ports are configured as a peer-to-peer network such that each device on the network is an equally privileged, equipotent participant node which can simultaneously function as both "clients" and "servers" to the other nodes on the network.

The design described herein facilitates activities such as cleaning and disinfection of the processor module, as housing contains no openings for fluids common in the hospital, such as water and blood, to flow inside. During a cleaning process the housing may simply be detached from the cradle and then cleaned. In addition, wear components, such as the tabs described above, can be provided on the cradle such that the majority of wear components are located on an inexpensive disposable unit while the relatively more expensive electronic components provide for multiple uses. Finally, the peer-to-peer architecture permits each node to communicate with, and so synchronize as necessary, with the other nodes available on the system.

In a first aspect, the invention provides a body-worn physiological data processing system, comprising:

a housing supporting electronic circuitry, the housing providing a waterproof enclosure for the electronic circuitry, the electronic circuitry comprising:

one or more processors configured to receive data from, and export data to, one or more peripheral devices external to the housing, and to use data received from one or more peripheral devices provide signals in deriving a measurement of at least one physiological property of the wearer, a display operably connected to the processor to display data received by the processor from one or more of the peripheral device(s), or a processed form thereof, a power supply operably connected to the processor and display, and one or more electrical contacts proximate to one or more openings in the housing and operably connected to the processor to provide one or more connections through which the processor receives data from, and exports data to, the one or more peripheral devices; and (b) a base, or "cradle," configured to releasably receive the housing, wherein when the housing is inserted into the base, one or more interface cavities are formed between the base and the housing.

wherein each interface cavity is adapted to establish an operable connection between one of the peripheral device(s) and the processor through a data cable connected to the peripheral device by insertion of a connector on the data cable into the interface cavity such that electrical contacts on the connector interconnect with a corresponding electrical contact on the housing, The base and housing can be mated with a positive latch, or may be mated by a simple friction fit, or by a combination of these. In the case of a friction fit, the friction fit is preferably strong enough to prevent separation of the base and housing under the force of gravity. In certain embodiments, at least one interface cavity formed by mating of the housing and the base comprises a latch mechanism which acts to prevent separation of the base from the housing when a connector is inserted fully into the cavity. In preferred embodiments, this latch mechanism comprises at least one first recess in a wall of the interface cavity provided by the base, and at least one second recess in a wall of the interface cavity provided by the housing. The first and second recesses are configured to receive a portion of the connector when it is inserted which acts similarly to a latch bolt on a conventional lock to physically restrain separation of the base and housing until the connector is removed.

In certain embodiments, the base comprises a reclosable tape or retaining strap for reversibly fixing the data processing system to the wearer. In these embodiments, openings may be provided in the base through which such a strap can thread. Other alternatives for affixing the strap include bonding materials such as adhesives, ultrasonic welds, etc. The strap may comprise mated hook-and-loop patches or similar fastening elements such as tapes, snaps, buckles, etc., to secure the system to the wearer's body during use.

Preferably, the base is designed as a disposable component which receives an electronics housing preferably designed for multiple uses. As used herein, the term "disposable" with regard to the base refers to the characteristic that the base may be disengaged from housing in the course of normal use by the user of the system such that the electronics may be easily separated from, and need not be discarded with, the base. This can serve to place the device components of the system most susceptible to wear and cleanability issues on a disposable unit, while retaining the more expensive electronic components on an easily cleanable and reusable unit.

As noted above, the housing provides a waterproof enclosure for the electronic circuitry contained within the housing. The IP Code system defined in international standard IEC 60529 classifies the degrees of protection provided against the intrusion of solid objects (including body parts like hands and fingers), dust, accidental contact, and water in electrical enclosures. Preferably, the housing meets IEC 60529-2004 IPX7 standards, which provides that ingress of water in harmful quantity shall not be possible when the enclosure is immersed in water under up to 1 m of submersion for up to 30 minutes.

The connector may be held in the port by a friction fit, or may utilize a locking mechanism such as that of a standard RJ-45 modular connector which comprises a resilient tab which snap-fits into a recess on the housing. Removal of the connector is accomplished by simply pulling on the connector with sufficient force, or by disengaging the resilient tab from the recess prior to pulling. In preferred embodiments, a port can comprise a tab which exhibits a spring force and which flexes during insertion of a terminal end, and springs back when the terminal end is fully inserted for receiving and holding the cable in its proper orientation to establish data communication.

In certain embodiments, the processor is configured to derive a measurement of at least one physiological property of the wearer selected from the group consisting of heart rate, electrical activity of the heart, temperature, SpO2, blood pressure, cardiac stroke volume, cardiac output, motion, activity, posture, pulse rate, and respiration rate. Peripheral devices such as sensors to be connected to the system are selected appropriately for the physiological properties of interest. The peripheral devices which may be pluaggbly connected to the physiological data processing system may be selected from the group consisting of a body-worn optical probe adapted to measure at least one optical signal detected after interaction with the wearer's tissue, an accelerometer, a pump module configured to inflate a blood pressure cuff, an ECG sensor, an ICG sensor, and a temperature sensor. As noted, each peripheral device is adapted to establish an operable connection with the processor through a data cable connected to the peripheral device by insertion of a connector on the data cable into the interface cavity. This data cable can carry I/O signals to and from the peripheral, and preferably also provides power to one or more peripherals from a power supply contained within the housing. By powering a peripheral from the body worn housing, the peripheral may be made lighter, less expensive, and more readily disposable. It is not necessary that each peripheral be so powered; for example a first peripheral may be controlled and powered by the physiological data processing system, while a second peripheral may be controlled by the physiological data processing system but powered by its own on-board battery.

As noted above, the communications between the processor, sensors, and any other peripherals connected through the ports are configured as a peer-to-peer network such that each device on the network is an equally privileged, equipotent participant node which can simultaneously function as both "clients" and "servers" to the other nodes on the network. In preferred embodiments, the nodes communicate through a serial interface, or bus, operating on a controlled area network (CAN) protocol. The CAN bus, which is typically used in the automotive industry, allows different electronic systems to effectively and robustly communicate with each other with a small number of dropped packets, even in the presence of electrically noisy environments. This is particularly advantageous for ambulatory patients that may generate signals with large amounts of motion-induced noise.

In certain embodiments, the physiological data processing system comprises a transceiver for wirelessly communicating with a data acquisition system external to the body-worn physiological data processing system. In these embodiments, the necessary communications hardware may be provided within the housing, or may be external, e.g., provided as a "dongle" which pluggably inserts into one of the interface cavities formed by the housing and the base, or may be provided partially within the housing and partially externally. Provision of the communications hardware as an external pluggable component can provide additional flexibility in configuration for the end user.

The system may utilize one or more electronic connectors adapted to insert into an interface cavity and which act as "keys" to unlock menus within the processing system which are not otherwise available to the user. Examples of such key connectors include "mode connectors" which enable certain special modes including, but not limited to a sleep mode (disabling the system, for example during shipping), a manufacturer mode (permitting a manufacturer to interact with the system for calibration, servicing, etc.), a demo mode (permitting the unit to display a pre-programmed demonstration), and a biomedical mode (permitting a hospital or other care site access to settings generally not available to a patient).

Advantageously, the system may also utilize one or more non-electronic "dummy" connectors adapted to insert into an interface cavity which is not in operable use. These plugs can serve to protect the structures within an interface cavity and, in the case of a system utilizing connectors to provide a latch between the base and the housing, can serve as a latch when no electrically active connector is being employed by the user.

A number of additional features may be incorporated into the electronics contained within the housing. By way of non-limiting example, the display may provide a touch-screen interface for data entry to the processor; a microphone and speaker configured for two-way voice communication may be provided; a voice over Internet protocol (VOIP) communication protocol may be provided; etc.

Mis-connection of medical devices by medical workers due to the use of common connectors across different device types is increasingly understood as both a source of patient injury and damage to equipment. Thus, in certain embodiments, the interface cavity comprises a "key" structure, and the corresponding connector is adapted to match the key structure to reduce the risk of insertion of an incompatible connector into an interface cavity. For example, the base may comprise a raised element in the wall of the interface cavity which is matched by a recess in the appropriate connector. Incompatible connectors lacking the appropriate recess and interface dimension would be physically prevented from insertion. This description is by way of example only and is non-limiting on the types of lock-and-key structures which may be used.

In related aspects, the present invention provides a base configured to releasably receive a housing supporting a processor, wherein when the housing is inserted into the base, one or more interface cavities are formed between the base and the housing, each interface cavity comprising one or more electrical contacts on the housing operably connected to the processor, and each interface cavity adapted to receive an electrical connector which makes sliding contact with the electrical contacts within the interface cavity to establish an operable connection between a peripheral device and the processor, the base comprising:

a latch mechanism at a first end of the base, the latch mechanism comprising at least one recess in a portion of the base which forms part of a first interface cavity, said first recesses configured to receive a portion of the electrical connector when inserted;

a tab on a portion of the base which forms part of the first interface cavity, the tab configured to insert into a recess on the electrical connector when inserted and thereby position the connector into a recess on a portion of the housing which forms part of the first interface cavity;

a tab at a second end of the base which is configured to insert into a corresponding opening in the housing when mated thereto;

wherein insertion of the electrical connector into the first interface cavity so that the connector is positioned into the recess on the housing prevents separation of the base from the housing until the connector is removed.

Still other embodiments are found in the following detailed description of the invention, and in the claims.

DETAILED DESCRIPTION OF THE INVENTION

Figure 1:
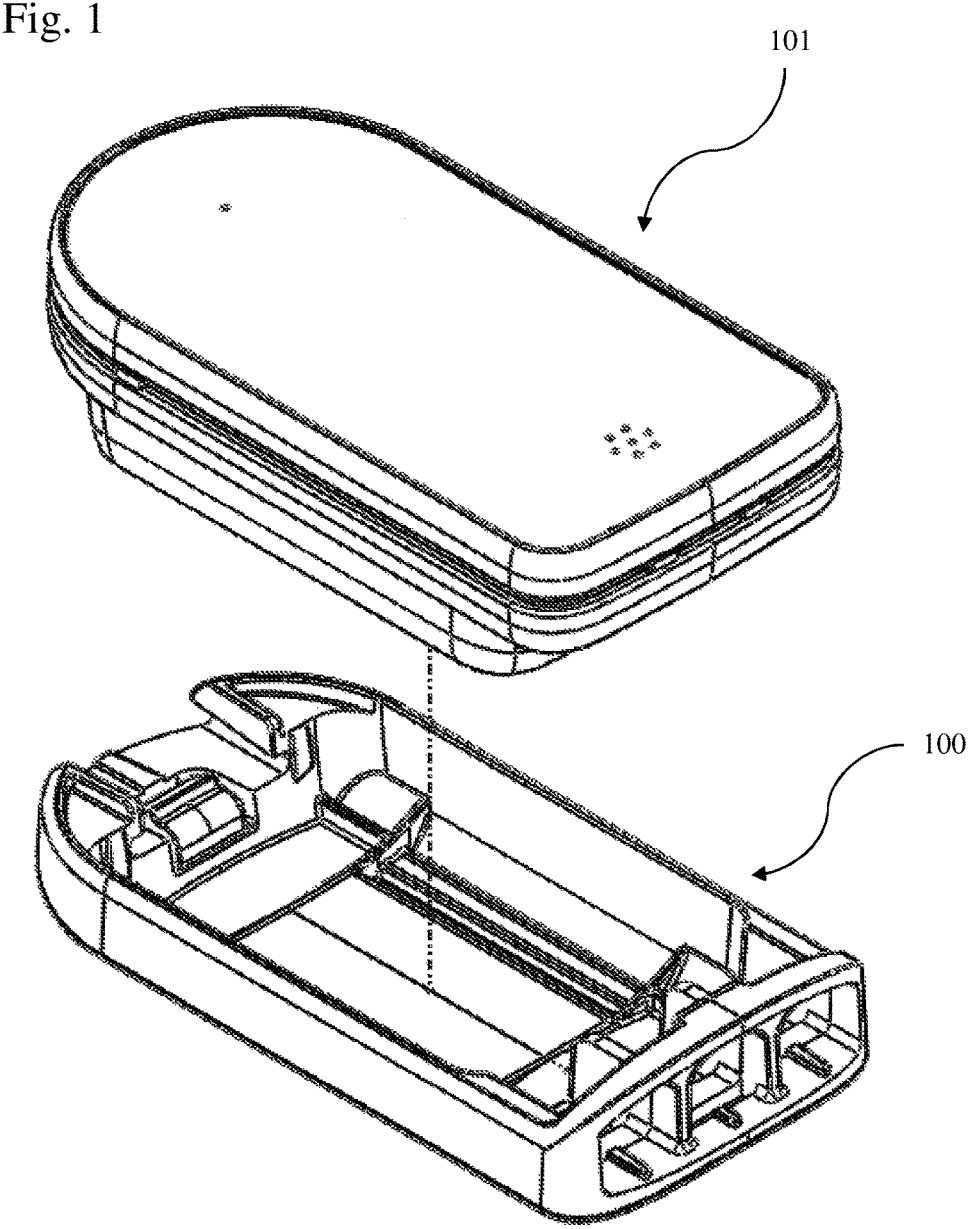
FIG. 1 shows a three-dimensional mechanical drawing of an exemplary processor module housing and base module of the present invention, depicting a mode of mating the processor module housing to the base module.
Figure 2:
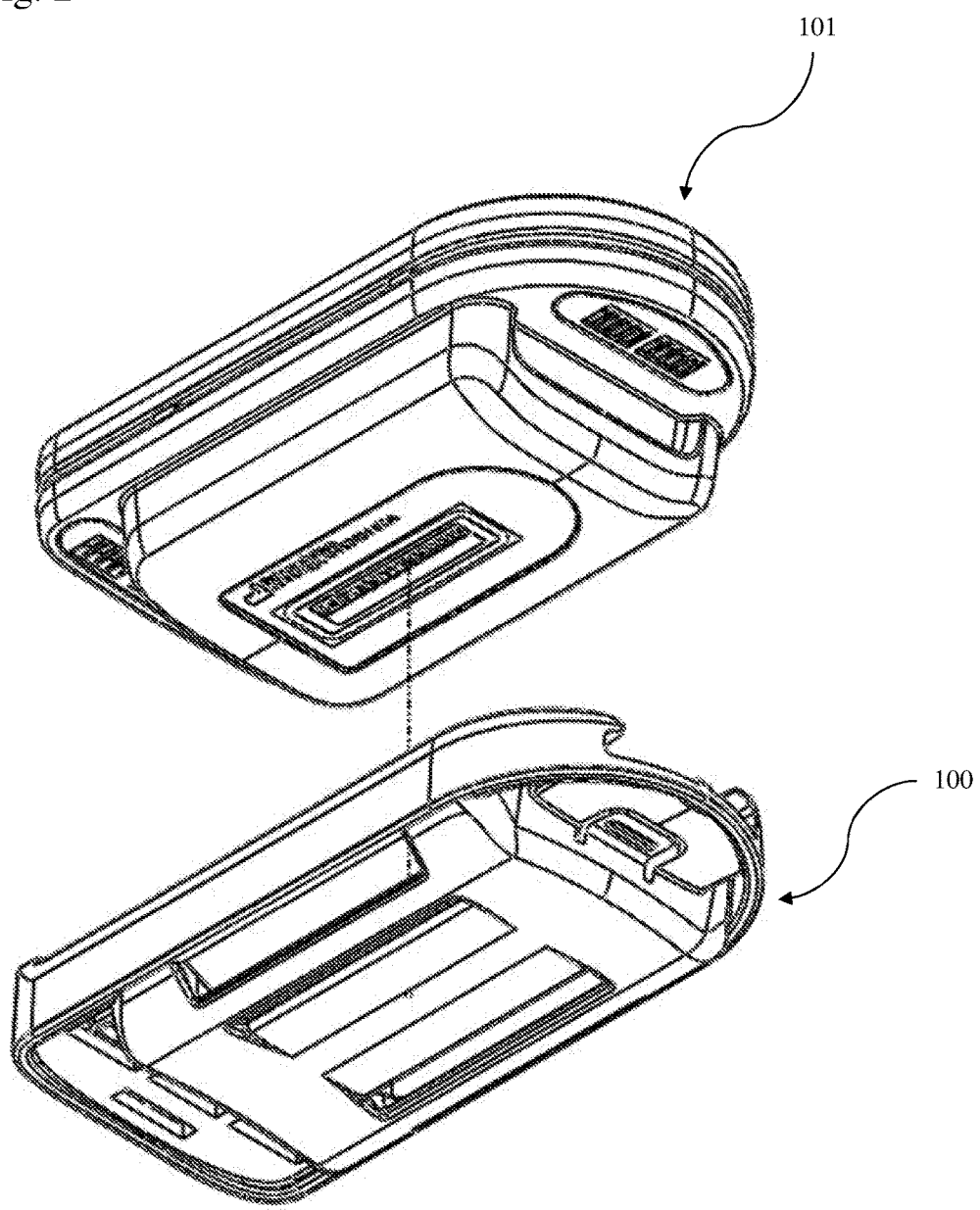
FIG. 2 shows an alternative view of a three-dimensional mechanical drawing of an exemplary processor module housing and base module of the present invention.

FIGS. 1 and 2 depict a top and bottom view of a base 100, and housing 101 which releasably attaches thereto, for use in the body-worn data processing system of the present invention. The housing provides a water-proof plastic casing housing a processor (the "system processor") and associated electronics (collectively the housing and the associated electronics being referred to herein as a "processing module"), and features openings on the underside that provide access to electrical interconnects that interface to connectors at the terminal ends of cables leading to the system's various sensors and other peripherals. In addition to being waterproof, this design facilitates activities such as cleaning and disinfection, as the housing contains no openings for fluids common in the hospital, such as water and blood, to flow inside.

The base is preferably designed as a disposable component which receives an electronics housing preferably designed for multiple uses. As used herein, the term "disposable" with regard to the base refers to the characteristic that the base may be disengaged from the housing in the course of normal use by the user of the body-worn data processing system such that the housing may be easily separated from, and need not be discarded with, the base. This can serve to place the system components most susceptible to wear and cleanability issues on a disposable unit, while retaining the more expensive electronic components in an easily cleanable and reusable unit.

During use, the housing reversibly snaps into the plastic base. Upon mating of the housing and the base, interface cavities, or "ports," are formed for receiving the terminal connectors of data cables leading to and/or from one or more peripheral devices such as sensors which collect data related to the physiological properties of interest. Insertion of a terminal connectors into such a port establishes electrical communication between the port's corresponding electrical interconnects and the cable, thereby permitting electrical communication between the system processor and the corresponding sensor or peripheral device. When mated, the housing and base are releasably attached; likewise, when a connector is inserted into a port, the connector and the port are releasably attached. As used herein, the terms "releasably attached" and "releasably receive" refers to two separate modules which may be engaged with and disengaged from one another in the course of normal use.

Figure 3:
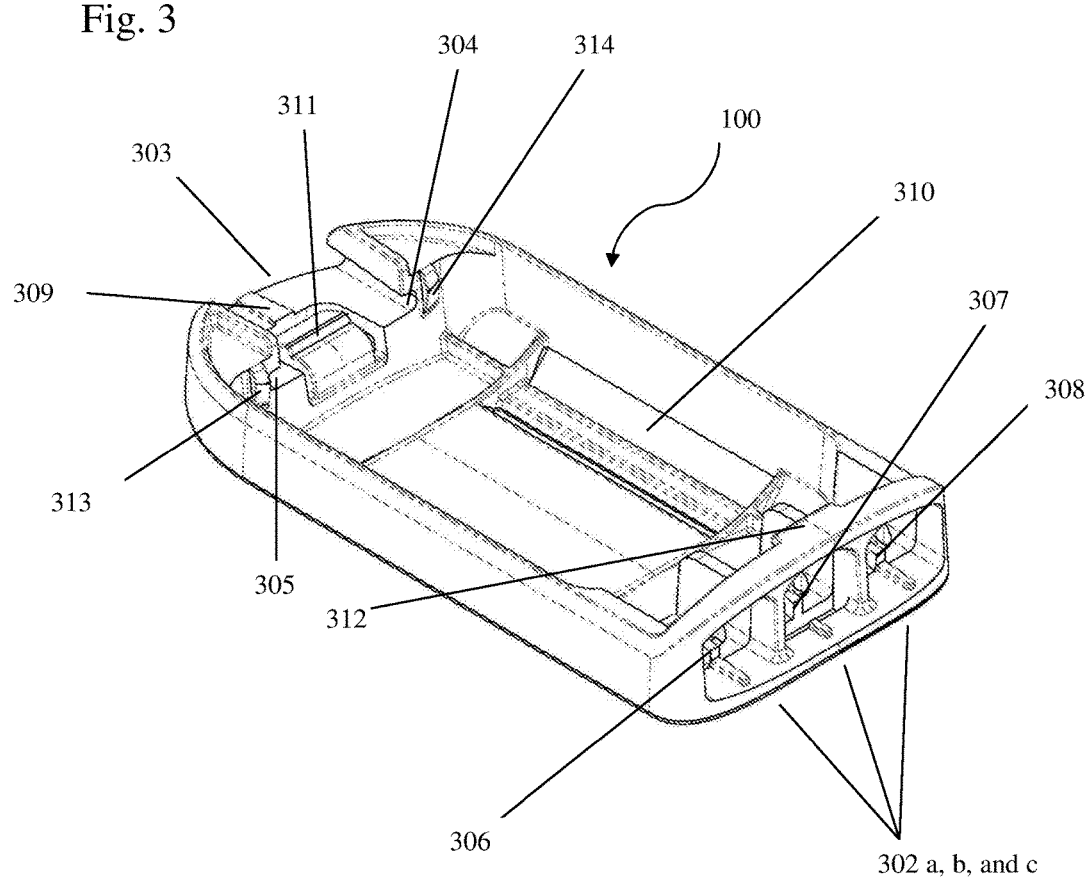
FIG. 3 shows a detailed view of a base module of the present invention.
Figure 4:
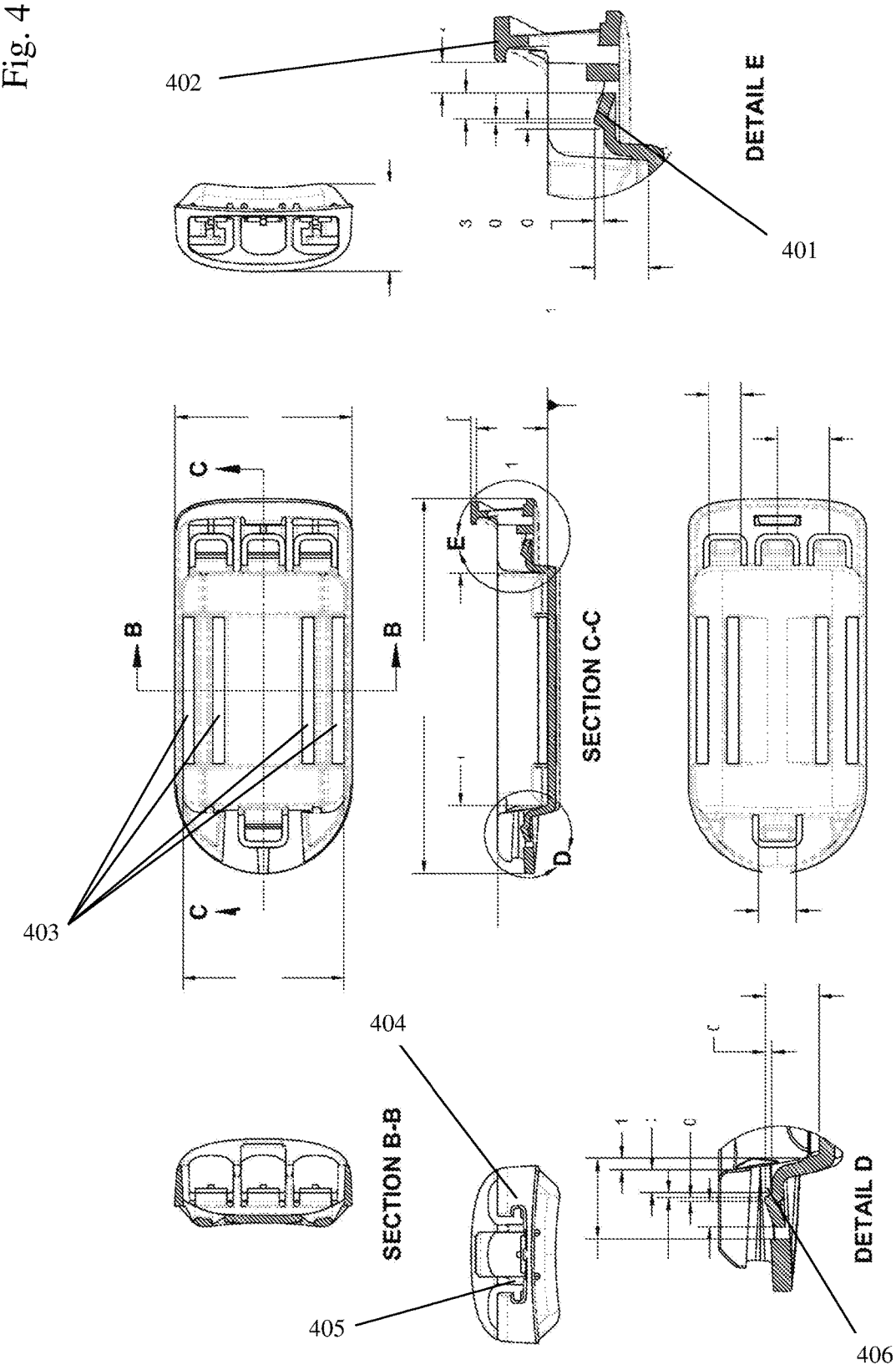
FIG. 4 shows a series of sectional views of the base module shown in FIG. 3.

FIGS. 3 and 4 depict base 100 in more detail. Openings 302 a, b and c positioned at a first end of the base, and a larger opening 303 positioned at a second end of the base, are configured to receive appropriately constructed terminal connectors, which are described in more detail below. The base provides a bottom wall and side walls for each interface cavity which receives a connector, while the waterproof electronics housing, when mated to the base, provides a top wall which includes electrical interconnects which are in sliding contact with the conductors of the terminal connector.

A tab 312 (also shown in cross section in FIG. 4, 402) fits into a groove in the housing to secure the first end of the base in the housing. Raised areas 313 and 314 at the second end of the base provide a friction fit for the housing; the tightness of this friction fit may be controlled by the thickness and flexibility of these raised areas. Preferably, the friction fit is sufficiently tight that the base can be inverted with the housing in place without the housing disengaging from the base.

Opening 303 (which in this example accommodates a terminal connector having 8 electrical interconnects) is capable of receiving a larger terminal connector than are openings 302 a, b and c (which each accommodate a terminal connector having 4 electrical interconnects). Opening 303 includes in its lateral walls recesses 304 and 305 (also shown in cross section in FIG. 4, 404 and 405). These recesses are configured to receive extensions (FIG. 6, 603 and 605) at the edge of the terminal connector when it is inserted into the interface cavity. A tab 311 that exhibits a spring force due to its material composition (thickness and stiffness of the material forming the tab) flexes during insertion of the terminal connector, and springs back when the terminal connector is fully inserted into the interface cavity.

Figure 8:
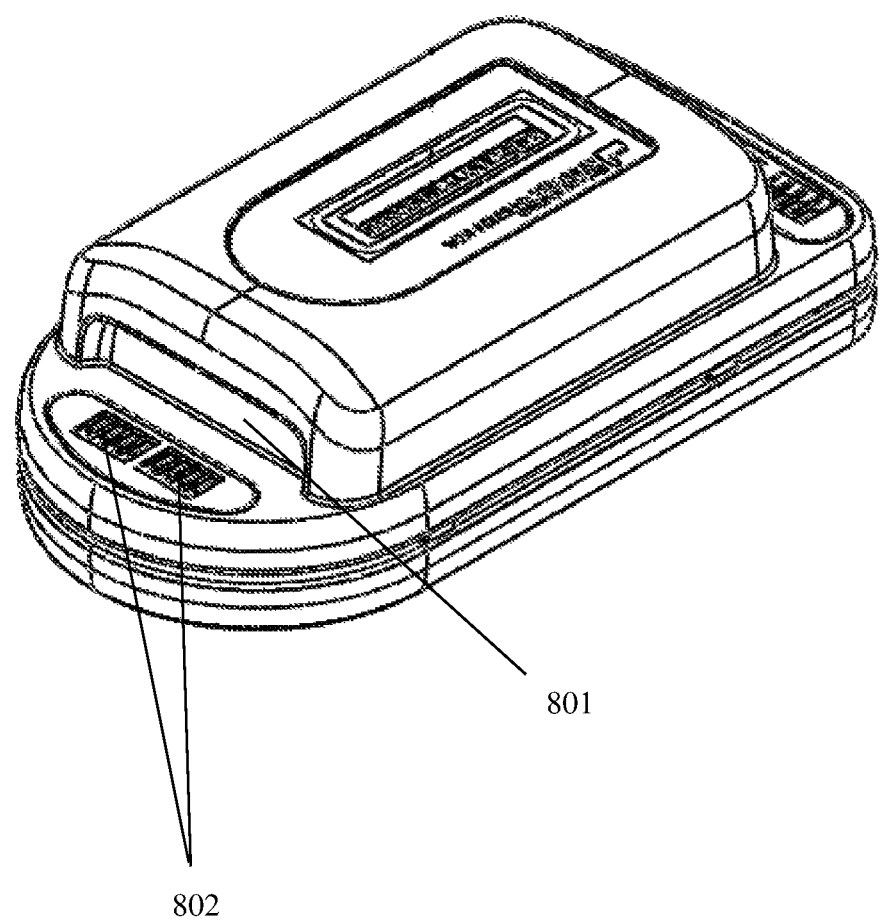
FIG. 8 shows a three-dimensional mechanical drawing depicting one view of a completed processor module housing of the present invention.

A raised portion of this tab (shown in cross-section in FIG. 4, 401) inserts into a depression in the bottom surface of the terminal connector (FIG. 6, 602), thereby forming a detent to provide positive location of the terminal connector when in its proper position. In this position, the electrical conductors of the terminal connector are in sliding contact with the corresponding electrical interconnects on the housing, and the distal end of the terminal connector (FIG. 6, 606) is inserted into a recess in the housing (FIG. 8, 801). So inserted, the housing is secured at one end by tab 312, while at the other end the terminal connector 600 forms a "deadbolt" lock due to insertion of its distal end 606 into recess 801 and insertion of extensions 603 and 605 into lateral walls recesses 304 and 305. This "latch" prevents removal of the housing from the base until the terminal connector 600 is removed. Once the terminal connector is removed, the base and housing may be separated by simply lifting the housing from the base.

Figure 5:
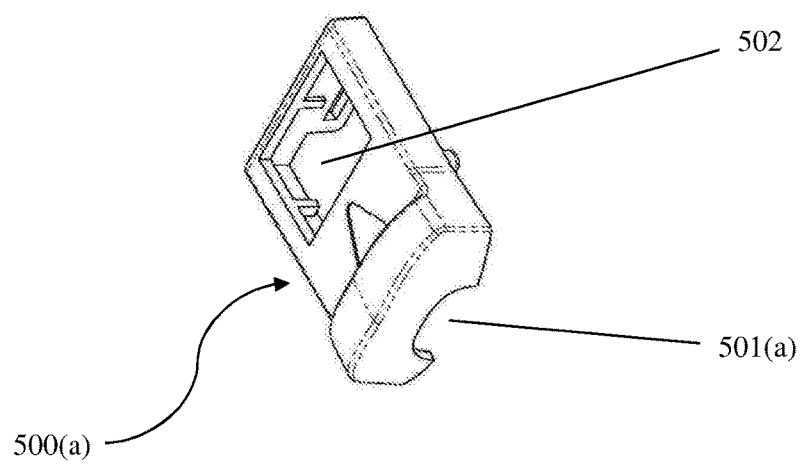
FIG. 5 shows a three-dimensional mechanical drawing depicting the top and bottom halves of an exemplary connector shell for use in the present invention.
Figure 5:
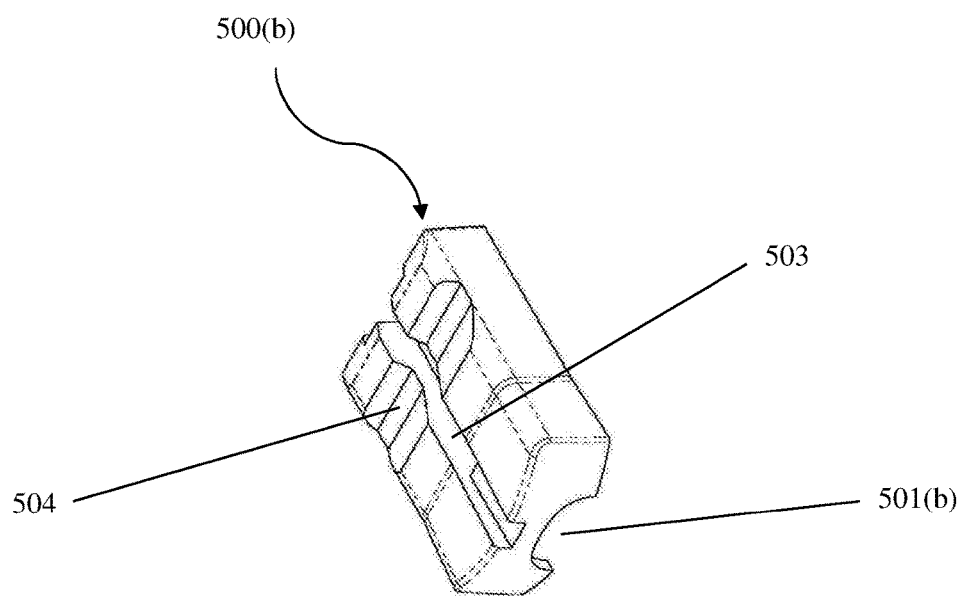

Like opening 303, each of openings 302 a, b, and c also contain a tab that flexes during insertion of the terminal connector, and springs back when the terminal connector is fully inserted into the interface cavity. A raised portion of this tab (shown in cross-section in FIG. 4, 401) inserts into a depression in the bottom surface of the terminal connector (FIG. 5, 504) to form a detent to provide positive location of the terminal connector when in its proper position. In this position, the electrical conductors of the terminal connector are in sliding contact with the corresponding electrical interconnects on the housing. These connectors, however, do not participate in the "latch" mechanism.

Figure 6:
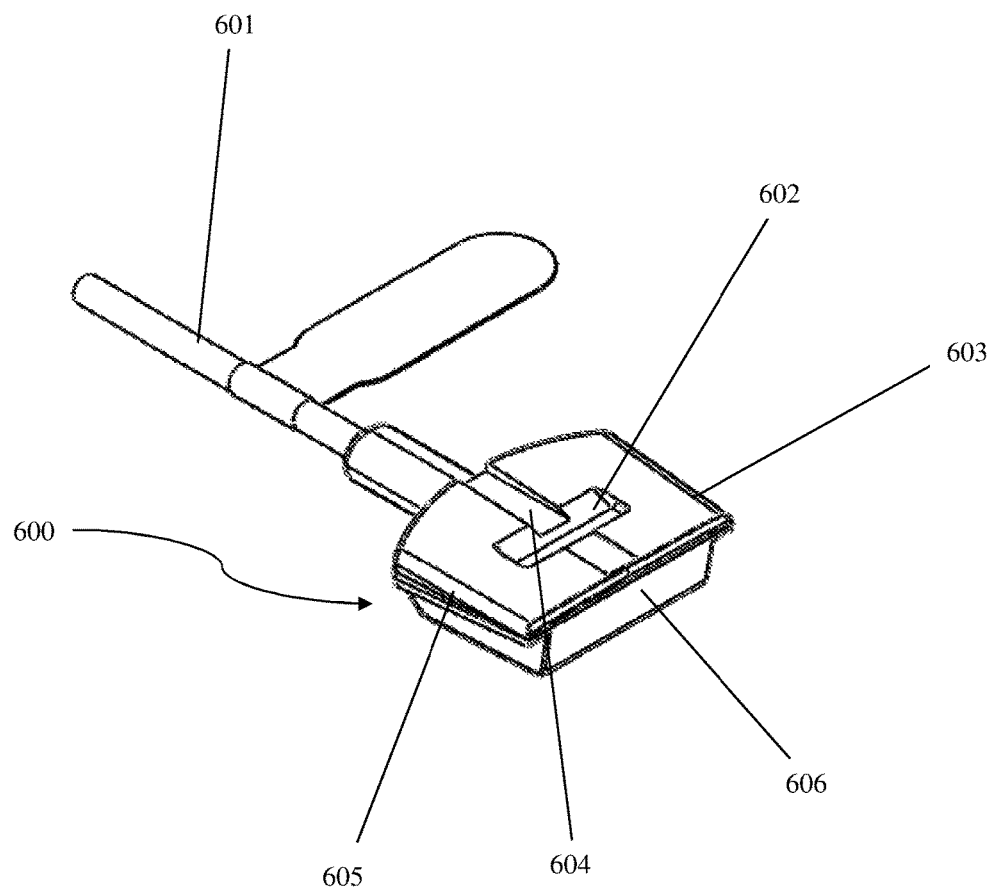
FIG. 6 shows a three-dimensional mechanical drawing of a completed connector for use in the present invention.

Raised posts 306, 307, 308, and 309 in each interface cavity provide a keying mechanism to prevent inadvertent insertion of an incompatible terminal connector. Each terminal connector has a corresponding slot (FIG. 5, 503; FIG. 6, 604) which is adapted to receive the raised post. A similarly sized connector lacking this slot would be prevented from insertion. It is preferred that this keying mechanism be unique as compared to other electrical cable connectors used in the particular care setting to limit chances for inadvertent insertion of an incorrect cable connector.

To affix the base to a wearer, slots (FIG. 3, 310; FIG. 4, 403) are provided through which a strap may be threaded. This strap may be sized according to the body location to which the base is to be affixed. A preferred site is the wrist of the wearer.

FIGS. 5A and B show the top and bottom halves of a data cable connector 500 configured to insert into one of openings 302 a, b, and c without the associated cable hardware. An opening 501 allows the cable leads to pass into the connector, and spring-tension "sliding" or "wiping" electrical contacts (similar to those of a standard modular RJ-45 cable) are positioned in opening 502. The connector is conveniently made as a 2-piece component for ease of cable attachment. As noted above, slot 503 and detent recess 504 serve to position the connector in its proper orientation and in a compatible interface recess.

FIG. 6 shows the bottom surface of a completed data cable connector 600 configured to fit larger opening 303. Cable 601 extending from a peripheral (not shown) enters the connector at its proximal end, relative to distal end 606 which forms part of the latch mechanism described above. Spring-tension "sliding" or "wiping" electrical contacts are positioned on the top surface of the connector (not shown). In some cases, it may be desirable to latch the housing and base together without the use of a data cable. In this case, a "dummy" connector lacking cable 601 and the associated wiring and electrical contacts may be provided. This dummy connector will comprise slot 604, detent recess 602, distal end 606, and extensions 605 and 603 to support insertion into opening 303. As in the case of connector 600, the dummy connector will provide a latch preventing removal of the housing from the base until the dummy connector is removed.

Figure 7:
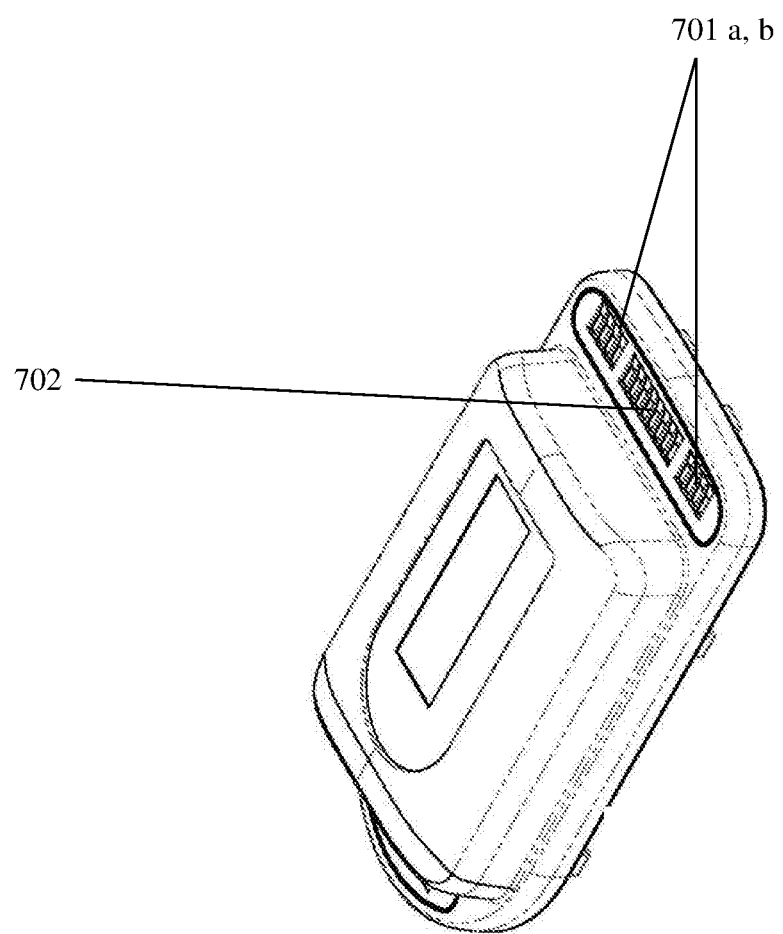
FIG. 7 shows a three-dimensional mechanical drawing depicting the bottom half of an exemplary processor module housing of the present invention.

FIGS. 7 and 8 show the underside of bottom portion of the housing. When mated to the base, contact pads 701 a and b and 702 overlay openings 302 a, b, and c in the base, thus forming the electrical interconnects that interface to the terminal connector at the end of cables. As noted above, openings 302 a, b, and c are sized to accommodate a connector having four electrical contacts, and contact pads 701 a and b contain a corresponding number of electrical interconnects. In contrast, contact pad 702 contains 8 electrical interconnects. The central four interconnects interface to the terminal end of a cable inserted into opening 302 b, and when the housing is mated to the base, the other four electrical connectors are unavailable. However, when the housing is separated from the base, these additional four contacts can provide for additional electrical access to the electronics within the housing. These additional four contacts can be used, for example, for battery charging, and a separate battery charging station which is adapted to receive the housing can be provided for this purpose.

Figure 9:
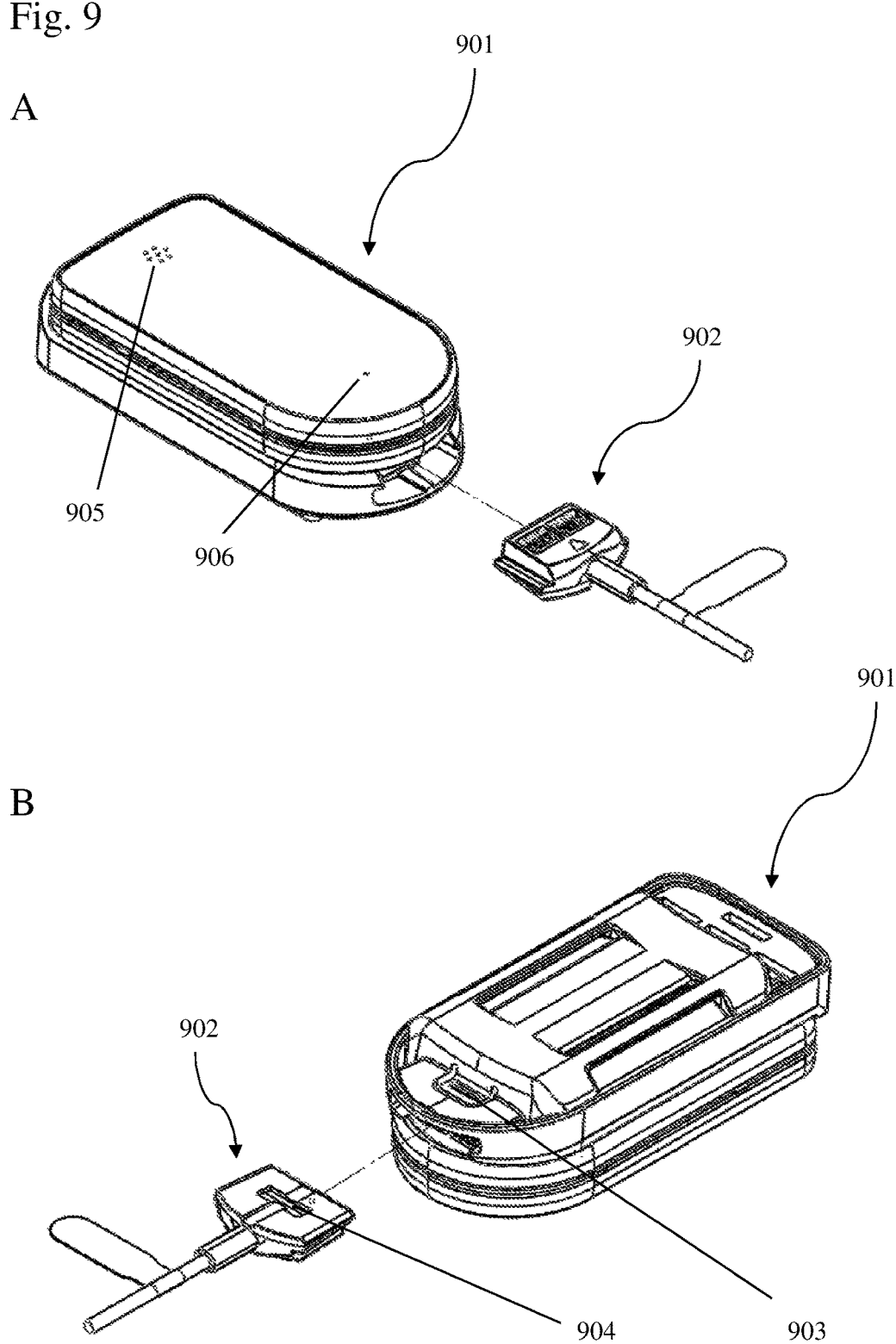
FIG. 9 shows a pair of three-dimensional mechanical drawings depicting the mode of insertion of a connector as shown in FIG. 5 into the mated processor module housing and base module as shown in FIG. 1.

Similarly, contact pad 802 overlays opening 303 in the base, thus forming the electrical interconnects that interface to the terminal connector of the larger cable. As discussed, opening 303 is sized to accommodate a connector having eight electrical contacts, and contact pad 802 contains a corresponding number of electrical interconnects. FIG. 9 depicts the releasable insertion of connector 902 into the interface cavity formed between opening 303 and contact pad 802 when the housing is mated to the base. Connector 902 is inserted until the detent depression 904 snaps into the ridge on tab 903. At this point, the distal end of the connector is inserted into recess 801, forming the latch which retains the housing in the base until the connector is removed.

Suitable electronics to be provided within the housing is described in detail in International Patent Application No. PCT/US2010/048866, International publication WO2010/135518, U.S. publication US20090018453A1, and U.S. publication US20100168589A1, each of which is hereby incorporated by reference in its entirety. The electronics preferably support serial communication through the CAN protocol. This allows the system processor to easily interpret signals that arrive from the various sensors, and means that the interface cavities need not be associated with a specific cable; any cable can be plugged into any compatible port. Furthermore, because the CAN protocol supports peer-to-peer connection of the peripherals, these peripherals may communicate directly with one another, for example for purposes of synchronization. Digital information generated by the attached peripherals can include a header that indicates the identity or origin of the signals so that the system processor can process them accordingly.

A variety of peripheral devices may communicate with the processing module. For example, a cable may transport I/O signals to/from an ECG circuit and electrodes; accelerometers; a cuff-based system for determining blood pressure values; a glucometer; an infusion pump, a body-worn insulin pump; a ventilator; an end-tidal CO2 monitoring system; a pulse oximeter or other optical physiological probe; and a thermometer. This list is not meant to be limiting. Using one or more of these inputs, the processing system can determine one or more physiological properties associated with the wearer, such as heart rate, electrical activity of the heart, temperature, SpO2, blood pressure, cardiac stroke volume, cardiac output, medication dosage, patient weight, blood glucose levels, end tidal $CO_2$, motion, activity, posture, pulse rate, and respiration rate.

The processing module can include a speaker and/or microphone that allows a medical professional to communicate with the patient, using an appropriate protocol such as a voice over Internet protocol (VOIP). For example, the medical professional can query the patient from a central nursing station; the electronics carried within the housing may function much like a conventional cellular telephone or 'walkie talkie': the processing module can be used for voice communications with a medical professional and can additionally relay information describing the patient's vital signs and motion. The processing module can be configured via software to support speech-to-text annotations. By this is meant that speech generated externally can be converted into text for display on the processing module, and/or speech generated at the processing module can be converted into text at an external computer.

The system processor is preferably operably connected to a data input device such as a keypad or touchscreen located at the top of the housing to permit the wearer or medical personnel to interact with the system. Openings may be provided in the top of the housing for the speaker and/or microphone, as depicted in FIGS. 9, 905 and 906; in order to maintain water resistance (e.g., at an IPX-7 standard), these openings may be sealed from underneath with a waterproof but breathable material such as a GORE-TEX® membrane (W. L. Gore & Associates, Inc.).

The electronics within the housing preferably include a battery or other power supply. Numerous battery technologies are known in the art, including common alkaline batteries, oxyride batteries, lithium batteries, etc. There are three preferred battery technologies that could be employed: Nickel Cadmium (NiCad), Nickel Metal Hydride (NIMH) and Lithium Ion (Li-ion), and most preferred are Li-ion batteries.

The battery can be provided in a "hot swap" configuration so that the electronics' data, wireless connections, etc., are preserved after the battery change. For example, prior to the hot swap a battery-powered dongle operating a firmware program may be plugged into one of the interface cavities. After being plugged in, the dongle sends a packet formatted according to the CAN protocol to the system processor indicating that its battery is about to be replaced with one having a full charge. The system processor receives the packet, and in response stores in non-volatile memory information that is normally not present when a device is initially powered on. Alternatively this information can be temporarily transferred for storage to a data buffer on an external network, or on non-volatile memory associated with the dongle. Once this is complete, the system processor can signal that the battery may be replaced. The depleted battery, located on the bottom side of the housing, can now be replaced with a charged battery. After this operation is complete the system processor can be returned to its configuration before the battery swap.

The "hot swap" configuration may not be suitable for IPX-7 standard waterproofing of the housing. Thus, in an alternative, the processor module itself may be swapped, rather than the battery within the module. In this scenario, a first processor module currently in use should transfer its store of data about the wearer to a second replacement processor module. Advantageously, a "bumping" action can be used to transfer this data. To initiate a transfer, a person accesses a special "data transfer" mode on the first and second processor modules. Then the first and second processor modules are brought into contact with one another using a sideways "bumping" action. Sensors (accelerometers) within each processor module sense the bump, and a matching algorithm pairs processor modules that detected the same bump (in terms of time and force). If and only if the bump is confirmed on the two processor modules will the data be exchanged. Following data exchange, the second processor module replaces the first processor module on the wrist-worn base of the wearer, and the first processor module is cleaned and recharged for later use. The matching algorithm may run locally on the processing modules themselves, or may run externally on a separate network. In the latter case, the processor modules would communicate the bump characteristics to the external network for processing.

Preferably, the electronics of the system support wireless transfer of data from the system to an external monitor or network. For relatively short distance RF communications, Bluetooth, Bluetooth LE, ANT+, HomeRF, IEEE 802.11x (e.g., IEEE 802.11a/b/g/n), and IEEE 802.15.4 are well known exemplary standard communications protocols that may be used. For somewhat longer range data transfers, cellular telephone protocols such as CDMA, TDMA, GSM, WAP, 3G (e.g., 3GPP, W-CDMA, TD-SCDMA, HSPA+, EVDO rev B, and CDMA2000), and 4G (e.g., LTE advanced, IEEE 802.16m) may be employed. These lists are not meant to be limiting. The electronics supporting wireless communication can be contained within the housing, or may be connected in a pluggable fashion through one of the interface cavities. Moreover, peripherals may also communicate with the system processor wirelessly rather than through a data cable connected to an interface cavity.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

What is claimed is:

1. A method of affixing a body-worn physiological data processing system on an individual, the body-worn physiological data processing system comprising a housing supporting electronic circuitry and a base that mates with the housing, comprising:

securing the body-worn physiological data processing system to the arm of the individual with a reclosable strap affixed to the body-worn physiological data processing system, wherein (a) the housing provides a waterproof enclosure for the electronic circuitry meeting IEC 60529-2004 IPX7 standards, the electronic circuitry comprising:

a processor configured to receive data from, and export data to, one or more peripheral devices external to the housing, and to use data received from one or more of the peripheral device(s) in deriving a measurement of at least one physiological property of the wearer, a display operably connected to the processor to display data received by the processor from one or more of the peripheral device(s), or a processed form thereof, a power supply operably connected to the processor and display, one or more electrical contacts proximate to one or more openings in the housing and operably connected to the processor to provide one or more connections through which the processor receives data from, and exports data to, the one or more peripheral devices; and (b) the base is configured to releasably receive the housing, wherein when the housing is inserted into the base, one or more interface cavities are formed between the base and the housing, wherein each interface cavity is adapted to releasably receive a connector on a data cable connected to a peripheral device, thereby establishing an operable connection between the peripheral device and the processor through the data cable, wherein insertion of the connector on the data cable into the interface cavity interconnects electrical contacts on the connector with corresponding electrical contacts on the housing, and wherein at least one interface cavity comprises a latch mechanism comprising at least one first recess in a wall thereof provided by the base, and at least one second recess in a wall thereof provided by the housing, said first and second recesses configured to receive a portion of the connector when inserted, the insertion of the connector thereby preventing separation of the base from the housing until the connector is removed.

2. A method according to claim 1, wherein the system further comprises one or more peripheral devices independently selected from the group consisting of a body-worn optical probe adapted to measure at least one optical signal detected after interaction with the wearer's tissue, an accelerometer, an ECG sensor, an ICG sensor, and a temperature sensor, wherein each peripheral device is adapted to establish an operable connection with the processor through a data cable connected to the peripheral device by insertion of a connector on the data cable into the interface cavity.

3. A method according to claim 1, wherein the at least one physiological property is selected from the group consisting of heart rate, electrical activity of the heart, temperature, SpO2, blood pressure, cardiac stroke volume, cardiac output, motion, activity, posture, pulse rate, and respiration rate.

4. A method according to claim 1, wherein the electronic circuitry further comprises a transceiver operably connected to the processor for wirelessly communicating with a data acquisition system external to the body-worn physiological data processing system.

5. A method according to claim 1, wherein at least one interface cavity comprises a transceiver which is adapted to establish an operable connection with the processor by insertion into the interface cavity.

6. A method according to claim 1, wherein the interface cavity comprising a latch mechanism further comprises a tab on a surface of the base, the tab configured to insert into a recess on the connector when inserted and thereby position the connector into the second recess.

7. A method according to claim 1, further comprising a plug adapted to insert into an interface cavity which is not in operable use, wherein the plug is not electrically active.

8. A method according to claim 7, wherein the plug is adapted to insert into an interface cavity comprising a latch mechanism, the insertion of the plug thereby preventing separation of the base from the housing until the plug is removed.

9. A method according to claim 1, wherein the base comprises a tab at a first end thereof, which inserts into a corresponding opening in the housing when mated thereto, and wherein mating of the base and the housing forms an interface cavity comprising a latch mechanism distal to the end comprising the tab.

10. A method according to claim 1, wherein the display provides a touch-screen interface for data entry to the processor.

11. A method according to claim 4, wherein the electronic circuitry comprises a microphone and speaker configured for two-way voice communication.

12. A method according to claim 11, wherein the microphone and speaker are operably connected to the processor for voice over Internet protocol (VOIP) communication.

13. A method according to claim 1, wherein the base and strap are configured as a disposable unit.

14. A method according to claim 1, wherein the base comprises a key structure configured to prevent insertion of an incompatible connector into an interface cavity.

15. A method according to claim 1, wherein the base and the housing, when mated, engage one another by a friction fit having a strength sufficient to prevent separation of the base and the housing due to the force of gravity.

16. A method according to claim 1, wherein the reclosable strap is affixed to the base.

17. A method according to claim 1, wherein the strap comprises a hook-and-loop closure.

* * * * *